United States Patent
Svanberg

[11] Patent Number: 6,149,431
[45] Date of Patent: *Nov. 21, 2000

[54] DENTAL CURET AND SHARPENING MACHINE SYSTEM

[76] Inventor: Gunnar K. Svanberg, 5400 NW. 39th Ave., Gainesville, Fla. 32606

[*] Notice: This patent is subject to a terminal disclaimer.

[21] Appl. No.: 09/312,985

[22] Filed: May 17, 1999

Related U.S. Application Data

[60] Division of application No. 08/888,684, Jul. 7, 1997, Pat. No. 5,934,975, which is a continuation-in-part of application No. 08/174,653, Dec. 27, 1993, Pat. No. 5,645,468, which is a continuation-in-part of application No. 08/038,326, Mar. 29, 1993, abandoned, which is a division of application No. 07/726,618, Jul. 8, 1991, Pat. No. 5,197,227, which is a continuation-in-part of application No. 07/407,688, Sep. 14, 1989, Pat. No. 5,030,091, which is a continuation of application No. 07/092,887, Sep. 4, 1987, abandoned.

[51] Int. Cl.$^7$ ...................................................... A61C 1/00
[52] U.S. Cl. ............................................ 433/143; 433/144
[58] Field of Search ................................... 433/141, 142, 433/143, 144

[56] References Cited

U.S. PATENT DOCUMENTS

| | | |
|---|---|---|
| 1,138,355 | 5/1915 | Carr . |
| 1,350,951 | 8/1920 | Artmaier . |
| 1,605,320 | 11/1926 | Bates . |
| 2,114,757 | 4/1938 | Yerkes . |
| 2,366,671 | 1/1945 | Montelius . |
| 2,380,988 | 8/1945 | Mudler . |
| 2,544,097 | 3/1951 | Lentz . |
| 2,578,309 | 12/1951 | Kroczek . |
| 3,251,150 | 5/1966 | Sedgwick et al. . |
| 3,670,460 | 6/1972 | Oldfield . |
| 3,724,081 | 4/1973 | Windecker et al. . |
| 3,902,283 | 9/1975 | Bean . |
| 4,321,040 | 3/1982 | Miller et al. . |
| 4,535,570 | 8/1985 | Ochiai et al. . |
| 4,720,907 | 1/1988 | Rapp . |
| 4,988,295 | 1/1991 | Kline ........................................ 433/144 |
| 5,030,091 | 7/1991 | Svanberg ................................ 433/143 |
| 5,044,124 | 9/1991 | Niimura . |
| 5,584,691 | 12/1996 | Domanella ............................. 433/143 |
| 5,645,468 | 7/1997 | Svanberg . |
| 5,682,665 | 11/1997 | Svanberg ............................ 433/143 X |

FOREIGN PATENT DOCUMENTS

| | | |
|---|---|---|
| 0561283 | 9/1993 | European Pat. Off. . |
| 1495115 | 12/1977 | United Kingdom . |

OTHER PUBLICATIONS

Nordent Catalog No. 103 (1982) pp. 16–17.
"Hu–Friedy" MFG. Co. Inc. Catalog (1985) 4 pages.

*Primary Examiner*—Nicholas D. Lucchesi
*Attorney, Agent, or Firm*—Saliwanchik, Lloyd & Saliwanchik

[57] ABSTRACT

A dental curet and sharpening machine system has been developed for convenient, accurate, and rapid sharpening of dental curets. Curets comprising a cutting blade, shank, and handle have been designed so that, regardless of the instrument's rake angle, the arc center of the toe on the face of the cutting blade which is to be sharpened lies on the longitudinal center axis of the instrument and at a constant distance from reference means on the instrument handle. The sharpening machine comprises a base, a sharpening element, and an instrument guide unit. The instrument guide unit can position the blade face of a curet of any rake angle in a plane with the arc center of the toe on the blade's face coincident with an axis about which the guide unit can be swung while the blade is engaged with the sharpening element during the cutting procedure. The invention comprises three aspects: (1) the curets; (2) the sharpening machine; and (3) the method of sharpening the curets.

3 Claims, 19 Drawing Sheets

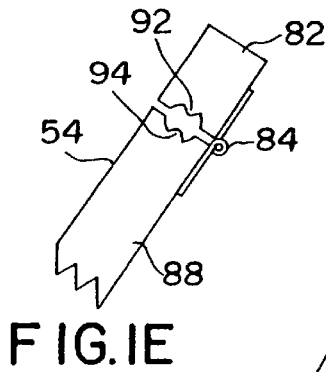
FIG. IE
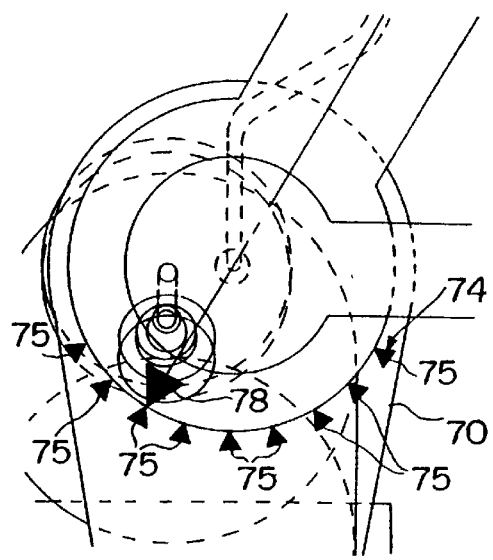
FIG. ID
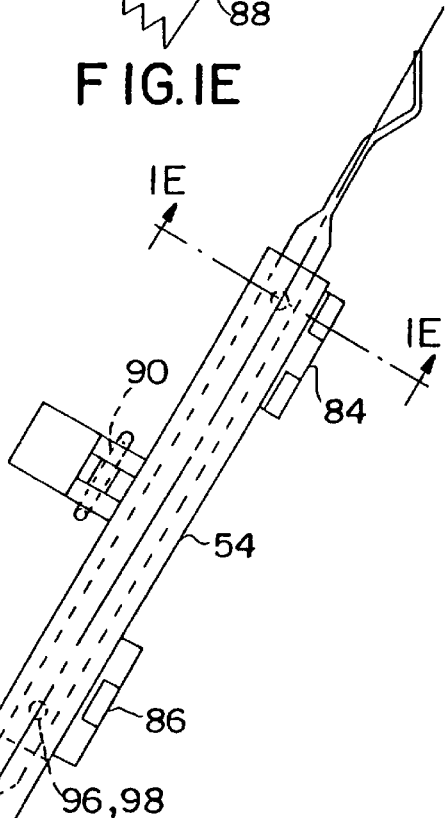
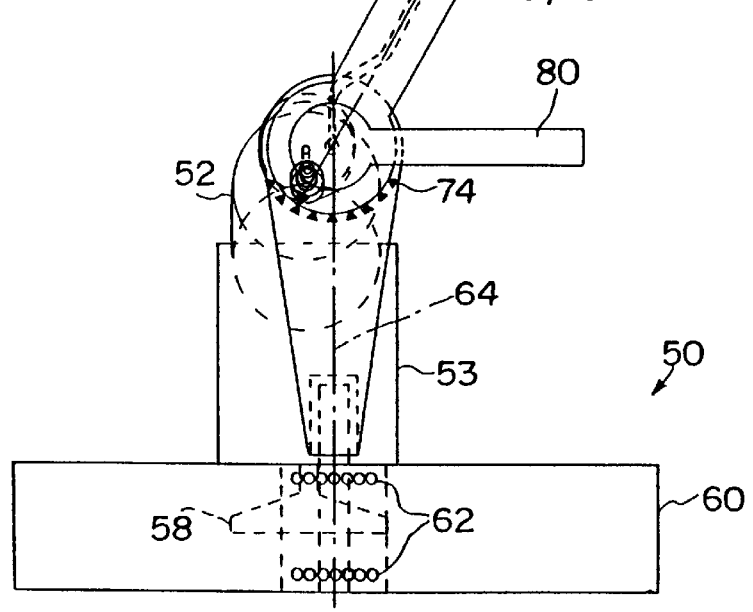
FIG. IA

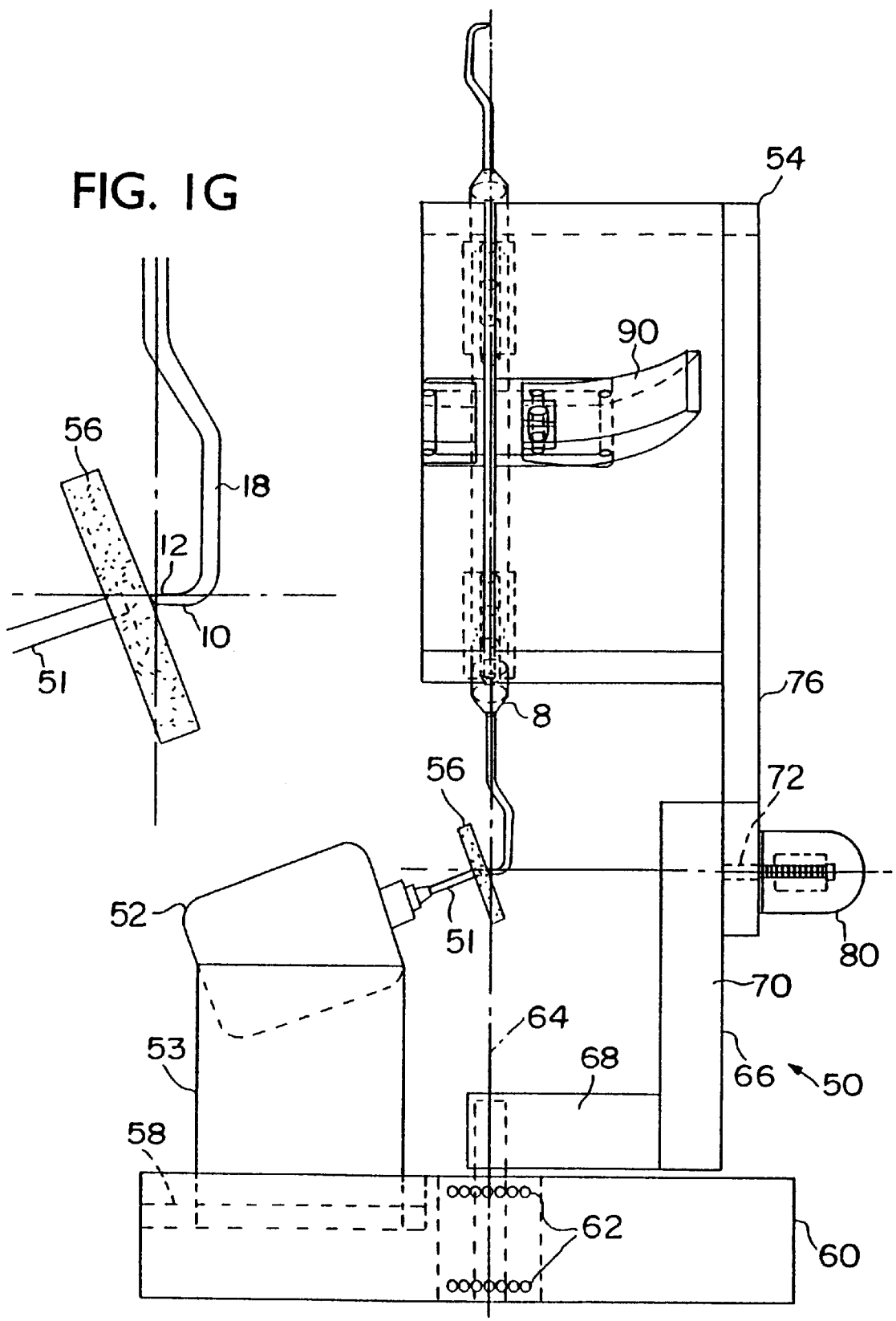

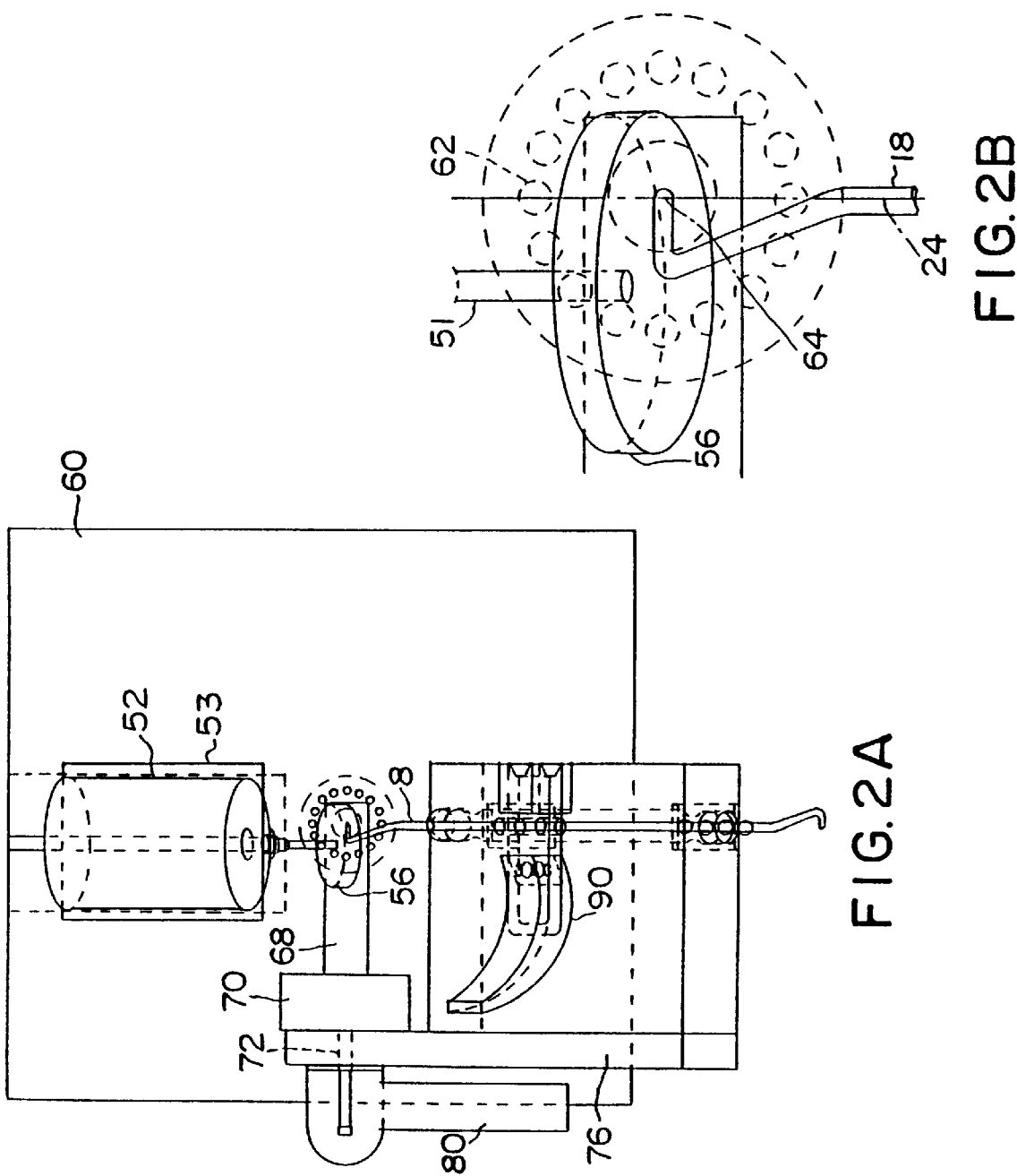

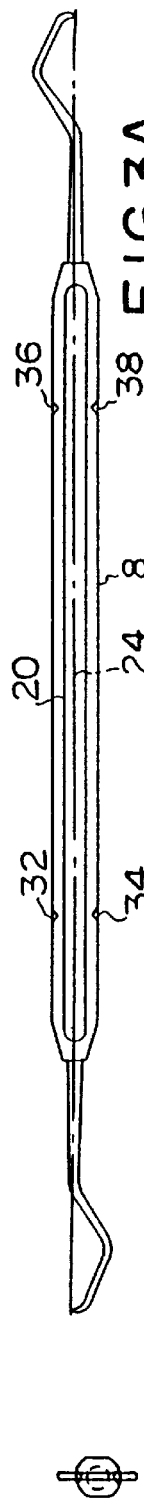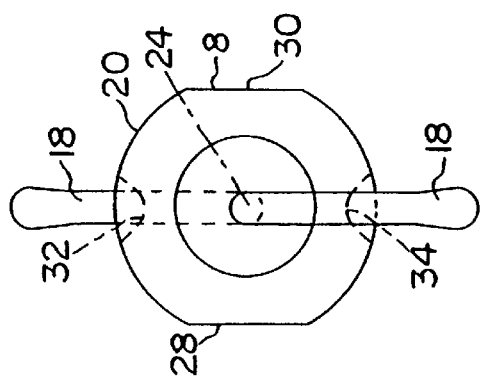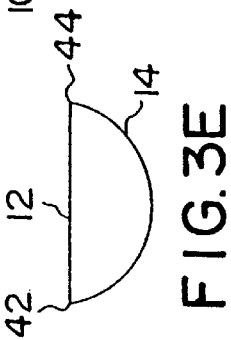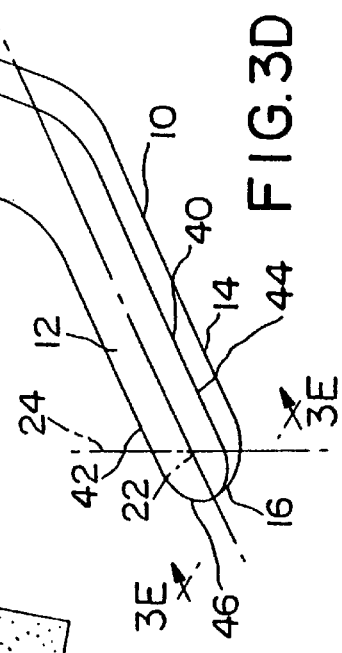

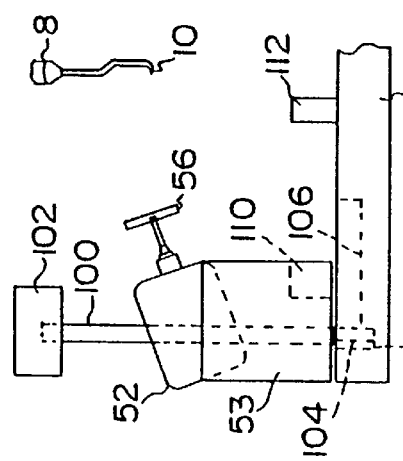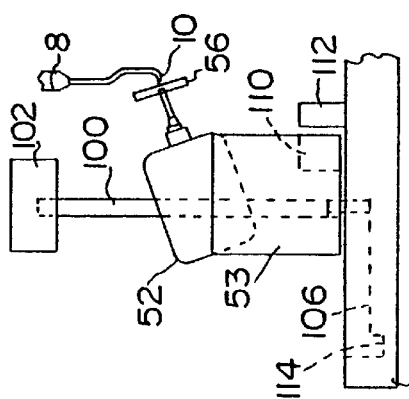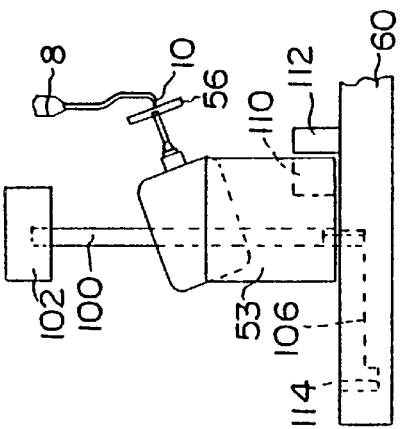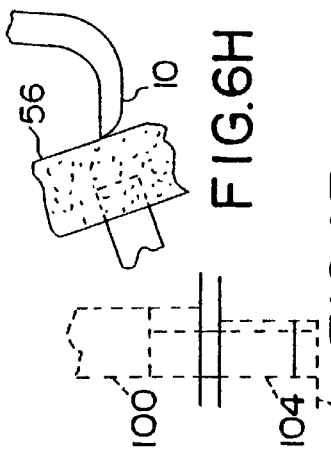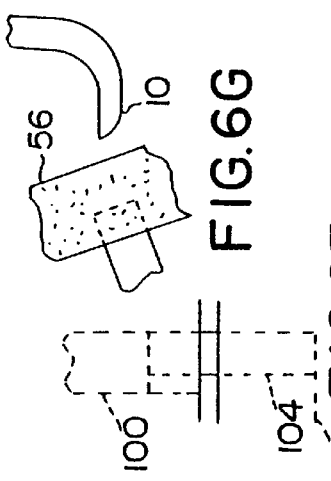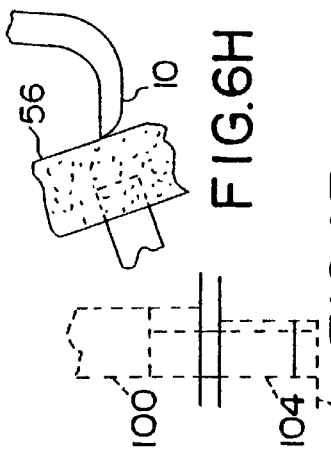

FIG. 7A

* Speed of rotation of stepping motor = 120Hz
* = Pulse time 8.3 mS

* RAM - memory
* 0 = Speed linear movement
* 1 = Counter of number of sharpenings
* 2 = Test rotation; right, left
* 3 = Determine mean current - sharpening element
* 11 = Analog comparison value - current sharpening element - side edge
* 12 = Counter - rotation - number of steps - without curet

```
Start current    EQU      40          *current - first contact
Add current      EQU      30          *value to add to "start current"
Number           EQU      7           *number - sharpenings
Time forward EQU          50          *time - sharpening element forward - high speed
Peo              EQU      $1031       *analog port in 0

ORG      $FFFE
                 FCB      $F8,0

ORG      $FF00       *timer in routine
                 INC      20
                 INC      21
                 INC      22
                 LDAA     #$80
                 STAA     $1025
                 RTI ORG      $FFDE       *timer int. vector
                 FCB      $FF,0
```
*****************************************************************************
```
                 ORG      $F800

LDS      #$FF        *start initiation program
                 LDY      #$1000
                 LDAA     #$80
                 STAA     $1024
                 CLI
                 LDAA     #$80
                 STAA     $100B
                 LDAA     #$60
                 STAA     $100C
                 LDAA     #$A0
                 STAA     $1020       *TCTL1
```

FIG. 7B

|       |            |              |                        |
|-------|------------|--------------|------------------------|
|       | CLR        | $1016        | *OC1                   |
|       | CLR        | $1017        |                        |
|       | CLR        | $101A        | *OC3                   |
|       | CLR        | $1018        | *OC2                   |
|       | LDAA       | #1           |                        |
|       | STAA $1019 |              |                        |
|       | STAA $101B |              |                        |
|       | LDAA       | #$80         | *start A/D converter   |
|       | STAA $1039 |              |                        |
|       | LDAA       | #$20         |                        |
|       | STAA $1030 |              |                        |
|       | LDAA       | #$F0         | *port C                |
|       | STAA $1007 |              |                        |
|       | LDAA       | #0           |                        |
|       | STAA $1003 |              |                        |
|       | CLR        | $1000        | *zero port A           |
|       | CLR        | $1003        | *zero port C           |

\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*

START MAIN PROGRAM

|        |            |                 |                               |
|--------|------------|-----------------|-------------------------------|
|        | LDAA       | #ANT            | *set - number -sharpenings    |
|        | STAA 1     |                 |                               |
|        | LDAA       | #1              | *realay R1                    |
|        | STAA $1004 |                 |                               |
|        | JSR        | TIME2           |                               |
| Wait   | BRSET      | 8,Y,#4,START    | *move sharpening element to   |
|        | LDAA       | #250            | *start position               |
|        | STAA 0     |                 |                               |
|        | JSR        | BACK            |                               |
|        | BRA        | WAIT            |                               |
| Start  | CLR        | 0               |                               |
|        | CLR        | 20              |                               |
|        | JSR        | FORW            |                               |
|        | BRCLR      | 3,Y,#1,START    | *test curet type              |
|        | JMP        | STARTH          |                               |
| Start  | BRSET      | 3,Y,#2,TRANS1   | *test translational movement  |
|        | JSR        | TRANSL          |                               |
|        | BRA        | TRANS2          |                               |
| Trans1 | JSR        | TRANSST         |                               |

FIG. 7C

| | | | |
|---|---|---|---|
| Trans2 | LDAA | #255 | *turn step meter to reference position |
| | STAA 10 | | |
| | JSR | TURNR | *start turn left |
| | | | |
| | LDAA | #25 | *turn step meter to start |
| | STAA 10 | | *sharp. el. out |
| | | | |
| | JSR | TURNL | *start rotation to |
| | LDAA | #250 | *sharp. el. |
| | STAA 0 | | *forward high speed |
| | JSR | FORW | |
| | CLR | 20 | |
| Time4 | LDAA 20 | | |
| | BRSET | 8,Y,#8,STOP | |
| | CMPA | #TIMEFORW | |
| | BCS | TIME4 | |
| | | | |
| | CLR | 20 | |
| Time5 | LDAA 20 | | |
| | BRSET | 8,Y,#8,STOP | |
| | CMPA | #TIMEFORW | |
| | | | |
| | BCS | TIME5 | |
| | | | |
| | LDAA | #50 | *sharp. el. forward |
| | STAA 0 | | *low speed |
| | JSR | FORW | |
| | | | |
| Lop | BRCLR | 8,Y,#8 | *sharpen |
| | | | |
| Stop | CLR | 0 | |
| | JSR | BACK | |
| | JMP | ADJST5 | *sharp. el. to home position |
| | | | |
| Sharpen | LDAA | PEO | *test tip |
| | CMPA | #STARTCURR | |
| | BCS | LOP | |
| | CLR | 0 | *stop forward movement |
| | JSR | FORW | |
| | | | |
| | CLRB | | *start sharpening |
| | ADDB | PEO | *seek |
| | JSR | TIME3 | *side edge |
| | ADDB | PEO | |
| | JSR | TIME3 | *take 4 readings |

FIG. 7D

```
        ADDB    PEO
        JSR     TIME3
        ADDB    PEO

LSRB            *divide by 4
        LSRB
        ADDB    #ADDCURR  *comparison value
        STAB    11              *analog value + 20
        LDAA    #30
        STAA 12                 *number of tries before stopping
                                *sharpening cycle
OK1     DEC     12
        BNE     OK2
        JMP     ADJST5
OK2     INC     10              *turn 1 step, wait
        JSR     TURNR           *measure and compare
        JSR     TIME
        LDAA    PEO
        ADDA    PEO+2
        LSRA
        CMPA    11
        BCS     OK1

LDAA    #75             *move sharp. el forward
        STAA 0                  *measure for 0.5 sec.
        JSR     FORW            *before rotation begins
        JSR     TIME2
        CLR     0
        JSR     BACK OK3     LDAA    #200            *sharpen over 180 degrees
        STAA 10                 *back and forth

JSR     TURNL

JSR     TIME4           *sharpening time, side edge

LDAA    #200
        STAA 10
        JSR     TURNR

JSR     TIME4           *sharpening time side edge
        DEC     1
```

FIG. 7E

```
            BEQ         END1
            LDAA        #3
            CMPA        1
            BNE         OK3
            LDAA        #200
            STAA 0
            JSR         BACK
            BRA         OK3

End1        JMP         ADJST5
```

********************************************************************

OTHER END OF CURET

```
StartR      BRSET       3,Y,#4,TRANS1B      *test transl. movement
            JSR         TRANSR
            BRA         TRANS2B
Trans1B     JSR         TRANSST
TRANS2B     LDAA        #255                *rotate step motor to ref. position
            STAA 10
            JSR         TURNL               *start rotation left LDAA        #25                 *rotate step motor to start sharp. el.
            STAA 10                         *out JSR         TURNR               *start rotation to
            LDAA        #250                *sharpening el.
            STAA 0                          *forward high speed
            JSR         FORW
            CLR         20
Time4B      LDAA        20
            BRSET       8,Y,#8,STOPB

CMPA        #TIMEFRW
            BCS         TIME4B

CLR         20
Time5B      LDAA        20
            BRSET       8,Y,#8,STOPB
            CMPA        #TIMEFRW
            BCS         TIME5B LDAA        #50                 *Sharp. el. forward
```

FIG. 7F

|  |  |  |  |
|---|---|---|---|
|  | STAA | 0 | *low speed |
|  | JSR | FORW |  |
| LopB | BRCLR | 8,Y,#8,SHARPB |  |
| StopB | CLR | 0 |  |
|  | JSR | BACK |  |
|  | JMP | ADJ5 | *sharp. el. to home position |
| SharpB | LDAA | PEO | *test tip |
|  | CMPA | #STARTCURR |  |
|  | BCS | LOPB |  |
|  | CLR | 0 | *stop forward movement |
|  | JSR | FORW |  |
|  | CLRB |  | *start sharpening |
|  | ADDB | PEO | *seek side edge |
|  | JSR | TIME3 |  |
|  | ADDB | PEO |  |
|  | JSR | TIME3 | *take 4 readings |
|  | ADDB | PEO |  |
|  | JSR | TIME3 |  |
|  | ADDB | PEO |  |
|  | LSRB |  | *divide by 4 |
|  | LSRB |  |  |
|  | ADDD | #ADDCURR | *comparison value |
|  | STAB | 11 | *analog value + 2 |
|  | LDAA | #30 |  |
|  | STAA 12 |  | *# of tries before discontinuation of *sharp. cycle |
| OK1B | DEC | 12 |  |
|  | BNE | OK2B |  |
|  | JMP | ADJST5 |  |
| OK2B | INC | 10 | *rotate 1 step, wait |
|  | JSR | TURNL | *measure and compare |
|  | JSR | TIME |  |
|  | LDAA | PEO |  |
|  | ADDA | PEO+2 |  |
|  | LSRA |  |  |
|  | CMPA | 11 |  |
|  | BCS | OK1B |  |
|  | LDAA | #75 | *move sharp. el. forward |

FIG. 7G

|        |         |         |                            |
|--------|---------|---------|----------------------------|
|        | STAA    | 0       | *measure for 0.5 sec       |
|        | JSR     | FORW    | *before rotation begins    |
|        | JSR     | TIME2   |                            |
|        | CLR     | 0       |                            |
|        | JSR     | BACK    |                            |
| OK3B   | LDAA    | #200    | *sharpen and rotate 180°   |
|        | STAA    | 10      | *back and forth            |
|        | JSR     | TURNR   |                            |
|        | JSR     | TIME4   | *sharpening time, side edge |
|        | LDAA    | #200    |                            |
|        | STAA    | 10      |                            |
|        | JSR     | TURNL   |                            |
|        | JSR     | TIME4   |                            |
|        | DEC     | 1       |                            |
|        | BEQ     | END1B   |                            |
|        | LDDA    | #3      |                            |
|        | CMPA    | 1       |                            |
|        | BNE     | OK3B    |                            |
|        | LDAA    | #200    |                            |
|        | STAA    | 0       |                            |
|        | JSR     | BACK    |                            |
|        | BRA     | OK3B    |                            |
| END1B  | JMP     | ADJST5  |                            |

*********************************************************************

STOP SHARPENING

|         |        |            |                         |
|---------|--------|------------|-------------------------|
| ADJST5  | LDAA   | #250       | *sharpening element     |
|         | STAA   | 0          | *to                     |
|         | JSR    | BACK       | *home position          |
| END     | BRCLR  | 8,Y,#4,END | *sharp. el wait         |
|         | CLR    | 0          | *stop linear movement   |
|         | JSR    | FORW       |                         |
|         | BCLR   | 4,Y,#1     | *in home position       |
|         | BRA    | END        | *relay off              |

SUBROUTINES

*SUBROUTINE TIME 60 mS ----------------------------------------------

TIME3      CLR       20
TIME12     LDAA      20
           CMPA      #2
           BCS       TIME12
           RTS

*SUBROUTINE TIME 100 mS ---------------------------------------------

TIME  CLR           20
TIME10     LDAA      20
           CMPA      #3
           BCS       TIME10
           RTS

*SUBROUTINE TIME 500 mS ---------------------------------------------

TIME4      CLR       20
TIME14     LDAA      20
           CMPA      #15
           BCS       TIME14
           RTS

*SUBROUTINE TIME 2 S ------------------------------------------------

TIME2      CLR       20
TIME11     LDAA      20
           CMPA      #100              *55
           BCS       TIME11
           RTS

*SUBROUTINE BACK MOVEMENT -------------------------------------------

BACK       CLR       $101A
           BCLR $D,Y,#$20
BACK1      BRSET     $D,Y,#20,BACK1
```

FIG. 7I

```
           BSET    $D,Y,#$40
           LDAA    0
           STAA    $1018
           RTS
```

*SUBROUTINE FORWARD MOVEMENT ----------------------------------------------

```
FORW       CLR     $1018
           BCLR    $D,Y,#$40,FORW1
FORW1      BRSET   $D,Y,#$40,FORW1
           BSET    $D,Y,#$20
           LDAA    0
           STAA    $101A
           RTS
```

*SUBROUTINE ROTATION LEFT
*STEPPING MOTOR

```
TURNL      BSET    4,Y,#2          *direction
           BSET    4,Y,#4          *pulse to motor LDX     #1000           *time between pulses WAIT1      CPX     #500
           BNE     STM2
           BCLR    4,Y,#4
STM2       DEX
           BNE     WAIT1
           DEC     10
           BNE     TURNL
           RTS
```

*SUBROUTINE ROTATION RIGHT ----------------------------------------------

*STEPPING MOTOR

```
TURNR      BCLR    4,Y,#2          *direction
           BSET    4,Y,#4          *pulse to motor
           LDX     #1000           *time between pulses
WAIT3      CPX     #500
           BNE     STM1
           BCLR    4,Y,#4
STM1       DEX
           BNE     WAIT3
           DEC     10
```

FIG. 7J

```
        BNE       TURNR
        RTS
```

*SUBROUTINE TRANSLATION LEFT ----------------------------------------------

```
TRANSL  BCLR   3,Y,#$80
        BSET   3,Y,#$40
        RTS
```

*SUBROUTINE TRANSLATION RIGHT ---------------------------------------------

```
TRANSR  BCLR   3,Y,#$40
        BSET   3,Y,#$80
        RTS
```

*SUBROUTINE TRANSLATION STOP ----------------------------------------------
```
TRANSST BCLR   3,Y,#$CO
        RTS
```

END

DENTAL CURET AND SHARPENING MACHINE SYSTEM

CROSS-REFERENCE TO RELATED APPLICATIONS

This is a divisional of application Ser. No. 08/888,684, filed Jul. 7, 1997 now U.S. Pat. No. 5,934,975; which is a continuation-in-part of co-pending application Ser. No. 08/174,653, filed Dec. 27, 1993 now U.S. Pat. No. 5,645,468; which is a continuation-in-part of application Ser. No. 08/038,326, filed Mar. 29, 1993, now abandoned; which is a division of Ser. No. 07/726,618, filed Jul. 8, 1991, now U.S. Pat. No. 5,197,227; which is a continuation-in-part of Ser. No. 07/407,688, filed Sep. 14, 1989, now U.S. Pat. No. 5,030,091; which is a continuation of application Ser. No. 07/092,887, filed Sep. 4, 1987, now abandoned.

BACKGROUND OF THE INVENTION

Scaling and root planing for the removal of calculus and contaminated root cementum are essential procedures in the treatment of periodontal diseases. For this purpose, dental curets are used for orthogonal cutting of the root surfaces, a method that removes thin chips of contaminated cementum.

This root planing procedure dulls the cutting edge of the curets which, for proper cutting action, have to be sharpened at frequent intervals. Up to now such sharpening action has been done as a free-hand procedure, with or without guide plates, resulting in edges of inferior sharpness and incorrect edge angles with serious aberrations from the ideal shape of the cutting blade. Although machines have been proposed to help in the process of sharpening curets, until now, no machine could accurately and efficiently produce a sharp cutting edge on any of a series of curets with different rake angles. See, for example, U.S. Pat. Nos. 1,350,951; 2,114,757; 2,578,309; 4,535,570; and 2,380,988.

A variety of dental curets of different shapes are available on the market, but there is no one single set of curets that in a systematic and logical way guides the operator in the selection of instruments needed for optimal efficiency in the different areas of the oral cavity. See, for example, U.S. Pat. Nos. 1,605,320; 1,495,115; 1,138,355; and 2,366,671.

Most curettes on the market are double-ended, i.e., comprise a longitudinal handle with a cutting blade at the distal end of a shank, which is secured to each end of the handle. The handles usually are made out of metal tubing, the surface of which is processed to give different patterns of groves and ridges to increase the friction when holding the curettes during the scaling and root planing procedures.

BRIEF SUMMARY OF THE INVENTION

The invention comprises dental curets and a sharpening machine having design features that make them integral parts of a dental curet and sharpening machine system that allows both professional and non-professional personnel to sharpen dental curets with the utmost precision. The system is unique in its use of reference means, placement means, and control means in an integrated manner that makes possible the fully guided and automatic procedure for sharpening curets. In one embodiment, which has control means comprising a central processing unit (CPU) with software stored in an erasable programmable read-only memory (EPROM), the subject invention pertains to an automatic curet sharpening machine that is able to automatically, accurately, and quickly sharpen the cutting edge of any one of a series of dental curets having different rake angles. In another embodiment, the invention pertains to the curets themselves having reference means, such as the shape and architecture of their handles or proximal part of the shanks, which facilitate specific placement of the curets in the sharpening machine. In addition, the curets can have a code, such as a color code, which relates to the rake angle of a particular curet. This code makes the identification of the instrument's rake angle easy, simplifies its placement in the sharpening machine, and indicates any need for an adjustment of the sharpening machine to produce a sharp cutting edge for any one of a series of curets having different rake angles.

Dental curets according to the subject invention are designed to provide a series of instruments with different rake angles in regular increments. According to the subject invention, the rake angle of each curet can be identified by a code, e.g. color code, which serves as a guide for the placement of the curet in the sharpening machine or a possible change in the setting of the machine's instrument guide unit. In addition, in a preferred embodiment of the subject invention, each curet has a reference means, such as marks on the handles and/or the geometry of the proximal portion of the shank, in a particular relationship to the cutting blades. The reference marks, or other reference means, are used to orient the curets in an instrument guide unit of the sharpening machine in a particular location so that the arc-center of the tip (also known as the toe) on the face of the cutting blade of the curet that is to be sharpened is in an axis around which the curet and/or the sharpening element rotate during the sharpening procedure.

Before the sharpening process begins, the curet is secured in a fixture portion of the instrument guide unit. Once the curet is secured within the fixture portion of the instrument guide unit, the curet does not move with respect to the fixture portion during the sharpening procedure. The fixture portion of the instrument guide has placement means that, in concert with the reference means, positions the flat surface at the arc-center of the cutting blade's tip perpendicular to the axis around which the instrument guide unit and/or the sharpening element rotates during the sharpening procedure, and at the same time the arc-center of the cutting blade's tip is in the axis around which the instrument guide unit and/or the sharpening element is rotating during the sharpening procedure. The placement means can consist, for example, of an upper portion (fixture portion that holds the curet) of the instrument guide unit. This fixture portion can pivot around an axis that is perpendicular to and runs through the axis around which the instrument guide unit rotates during the sharpening procedure thereby placing the face of the curet at the optimal position for sharpening. In another embodiment, the fixture portion has a plurality of locations at which a curet can be secured. Each such position would place a curet of a specific rake angle at the proper position for sharpening a curet of that rake angle. There may be, for example, about 7 to 15 different positions, each of which corresponds to a specific rake angle of a set of curets.

To achieve the sharpening of the entire cutting edge of the curet, the instrument guide unit (holding the curet in its fixture portion) must move relative to the sharpening element. As described herein, one of the preferred embodiments has the instrument guide unit pivot about a rotation axis while the sharpening element remains essentially stationary. Any architecture, shape, or geometry of the curets and/or sharpening machine serving to correctly position the curet in the sharpening machine are included within the spirit and scope of the subject invention.

The following description and illustrations exemplify one configuration of the dental curet and sharpening machine system. Other configurations would be apparent to those skilled in the art having the benefit of this disclosure. In a preferred embodiment, two sets of reference means can be contained on the handle of the double-ended curet. One set of reference marks is nearer to one blade, while the other set of reference marks is nearer to the other blade. The reference marks of each set are equidistant from the arc-center on the face of the nearer blade's semi-circular tip. Also, the longitudinal axis of the curet passes through the arc-center of the tip on the face of the cutting blade. When the curets are clamped in the fixture portion of instrument guide unit of the sharpening machine, the arc center on the face of the cutting blade is in a rotation axis around which the instrument guide unit and/or sharpening element rotate during the sharpening procedure. In one embodiment, the fixture portion of the instrument guide unit, which holds the curet, is moved by the placement means before the sharpening procedure begins. This movement of the fixture portion by the placement means is preferably around a second axis that is: (1) perpendicular to and running through the axis (the first axis) around which the instrument guide unit and/or sharpening element are rotating during the sharpening procedure; (2) aligned with the arc-center of the semi-circular tip on the face of the curet's cutting blade when the curet is secured in the instrument guide unit. This movement of the fixture portion is done to place the curet's cutting blade at the proper angle for sharpening, which is when the face at the arc-center of the semi-circular tip of the cutting blade is perpendicular to the axis around which the instrument guide unit and/or the sharpening element rotates during the sharpening procedure. This proper placement of the face of the curet for sharpening can also be accomplished using a fixture portion having multiple locations to place the curet. Each location is designed to place the face of the curet with a particular rake angle into the proper position for sharpening. Using, for example, a color code on the curets and the instrument guide unit, the flat face of the curet's cutting blade is oriented perpendicular to the rotation axis around which the instrument guide and/or the sharpening element is rotating during the sharpening procedure. This placement of the curet could be done using visual inspection to achieve the desired orientation of the face of the cutting blade; however, coded calibration is much preferred to obtain the greatest ease of operation.

The sharpening process involves contacting the curet cutting edge with a sharpening element. In a preferred embodiment, a sharpening element can be mounted on the shaft of an electric motor, which can be positioned along a guide in the base of the machine. The sharpening element can be disposed at a fixed angle relative to the face of the curet that is secured in the fixture portion of the instrument guide unit, which guarantees the restoration of a sharp cutting edge of the correct edge angle, when the motor is positioned to bring the sharpening element into contact with the blade. In one particular configuration, the instrument guide unit is rotated around a vertical rotation axis to cause the cutting edge to be passed against the sharpening element, first at one side of the blade, then along the semicircular shaped tip, and finally at the other side. As an alternative, the motor with the sharpening element could rotate around a stationary fixture holding the curet. Also, a combination of both the sharpening element and the instrument guide unit rotating could be used.

The sharpening machine of the subject invention provides complete guidance during the sharpening procedure. In a preferred embodiment, this guidance is achieved using control means. This control means can, for example, be an electromagnet having the appropriate power to bring the curet into contact with the cutting edge of the curet. Advantageously, the electromagnet system can include a rheostat that varies the power to the electromagnet, thereby adjusting the power of the magnet to ensure that a constant force per unit length of the cutting edge is applied.

The combination of these features makes it possible to sharpen curets with different rake angles by a simple adjustment of the sharpening machine as indicated by a suitable code, e.g. a color code, which relates to the rake angle of the curet to be sharpened, and also allows for the proper positioning of the curet using the placement means.

The foregoing features, advantages, and benefits of the invention, along with additional ones, will be seen in the ensuing description and claims which should be considered in conjunction with the accompanying drawings. The drawings disclose one of the preferred embodiments of the invention according to the best mode contemplated at the present time in carrying out the invention.

BRIEF DESCRIPTION OF THE DRAWINGS

FIGS. 1A, 1B, and 1C are, respectively, a front elevational view, a top plan view, and a side elevational view of a preferred embodiment of the dental curet and sharpening machine system of the invention.

FIG. 1D is an enlarged fragmentary view of a portion of FIG. 1A; FIG. 1E is a fragmentary cross sectional view in the direction of arrows 1E—1E in FIG. 1A; FIG. 1G is an enlarged fragmentary view of a portion of FIG. 1C.

FIG. 2A is a view similar to FIG. 1B but showing a different position; FIG. 2B is an enlarged view of a portion of FIG. 2A.

FIG. 3A is a longitudinal view of a curet shown by itself.

FIG. 3B is an end view of FIG. 3A; and FIG. 3C is an enlarged view of FIG. 3B.

FIG. 3D is a fragmentary perspective view of a curet blade.

FIG. 3E is an enlarged transverse view taken in the direction of arrows 3E—3E in FIG. 3D.

FIG. 3F is a fragmentary view in the same direction as FIG. 3E, but on a reduced scale and illustrating a step in the sharpening procedure.

FIGS. 3G and 3H together provide a fragmented view of the upper (18b) and lower (18a) portions of the shank of a dental curet.

FIGS. 6A, 6B, and 6C are fragmentary views illustrating a series of steps in the sharpening procedure for purposes of explanation.

FIGS. 6D1, 6E1, and 6F1 are close-up views of portions of FIGS. 6A, 6B, and 6C, respectively; and FIGS. 6D2, 6E2, and 6F2 are bottom end views of FIGS. 6D 1, 6E1, and 6F 1, respectively.

FIGS. 6G and 6H are close-up views of other portions of FIGS. 6B and 6C.

FIGS. 7a–7j show one example of a computer program which can be used according to one embodiment of the invention.

DETAILED DISCLOSURE OF THE INVENTION

The following description with illustrations of the integrated dental curet and sharpening machine system is only one of many possible configurations contemplated according to the subject invention. This description of a preferred embodiment serves to exemplify the underlying principles of the invention, the key features being the reference means, which enable the operator to secure a curet into the fixture portion of the sharpening machine in an exact orientation necessary for precision sharpening; and the placement means, which enable the machine to sharpen any one of a series of curets with different rake angles. In one preferred embodiment, the placement means comprises the instrument guide unit fitted with a movable fixture portion. A person skilled in this art, having reference to the descriptions contained herein, would readily appreciate that there are a variety of reference means and placement means which can be utilized to carry out the functions described herein. Any architecture, shape or geometry of these design features that will serve the same purposes are claimed in this application.

Figure 1B:
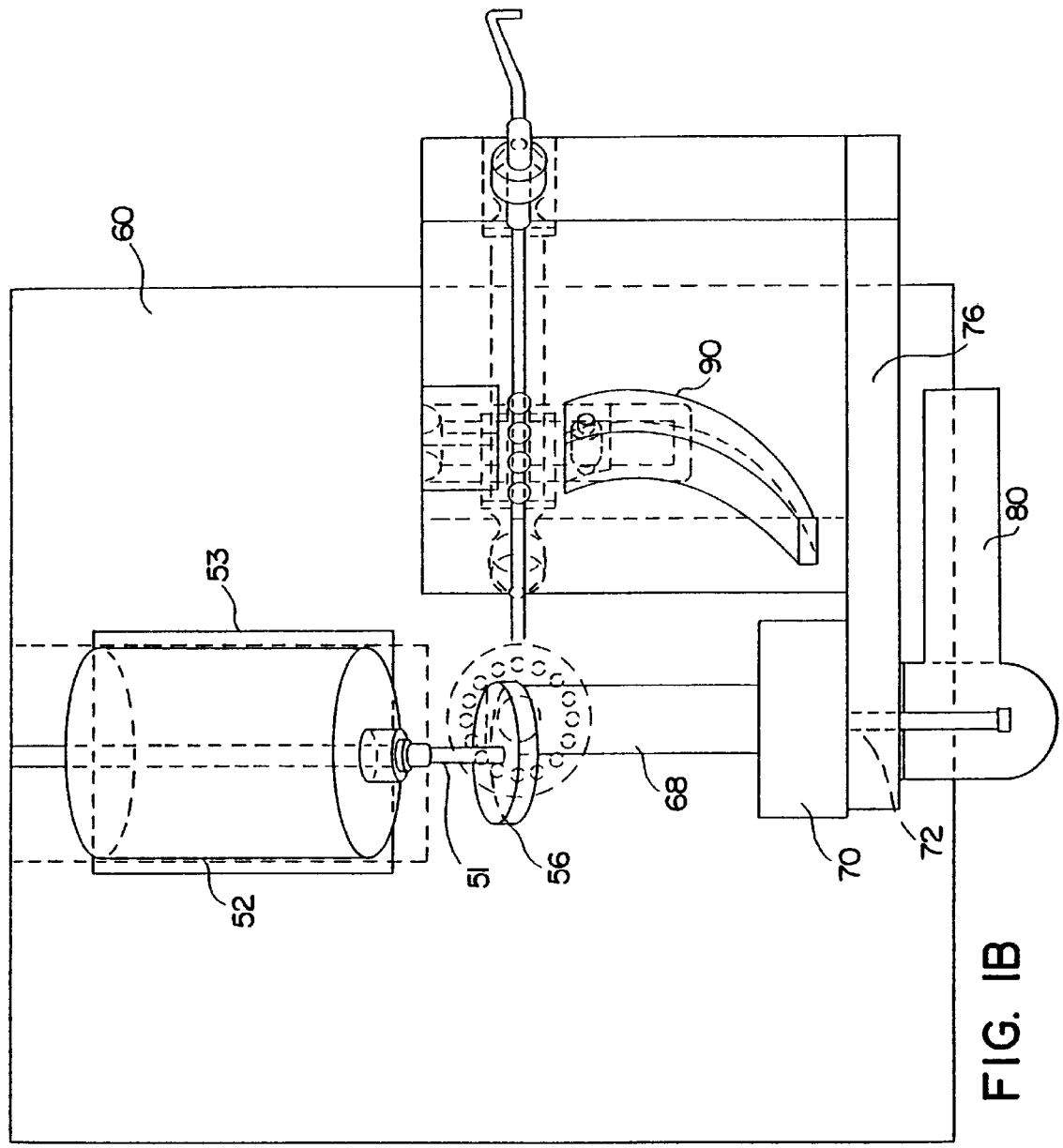
Figure 1F:
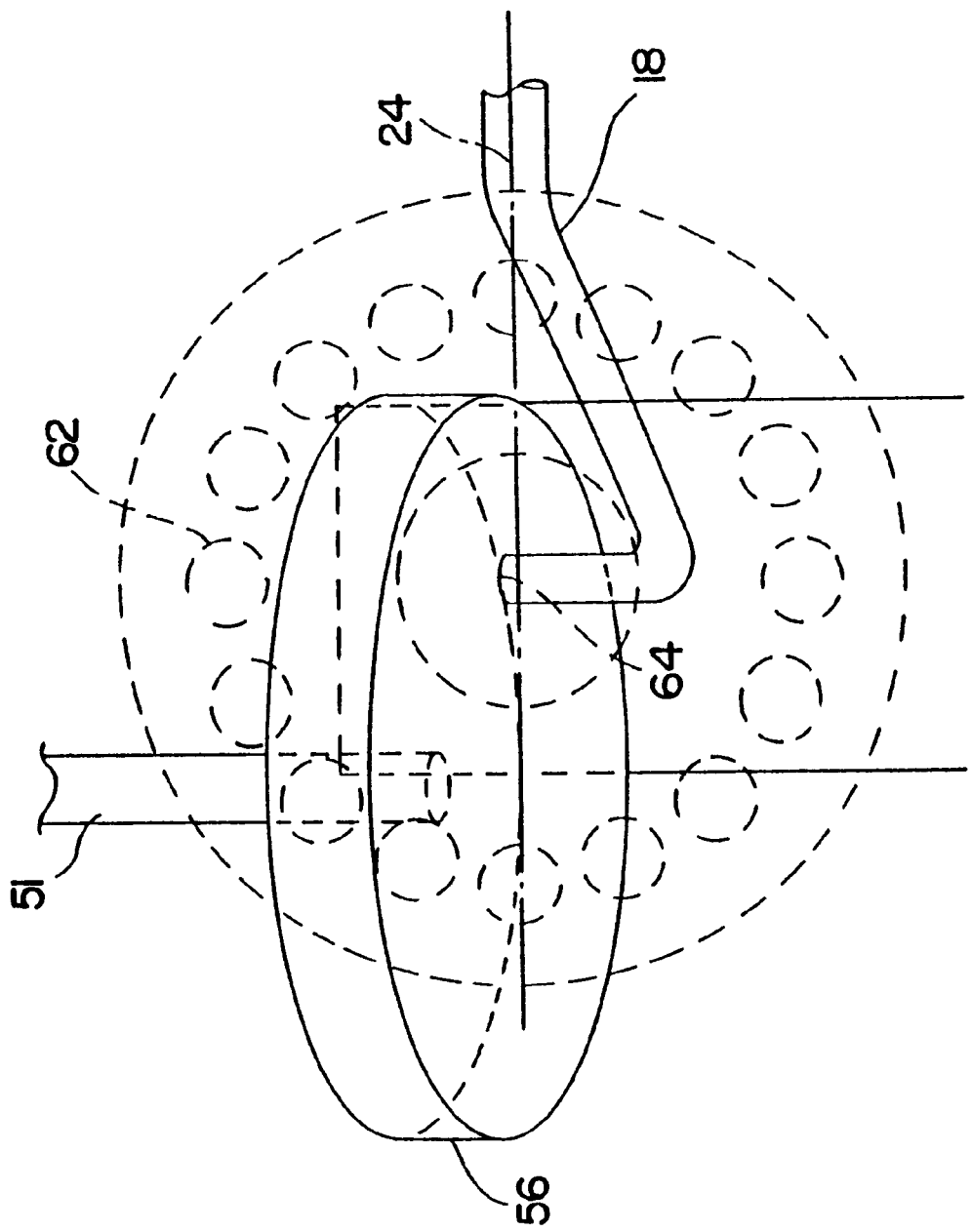
FIG. 1F is an enlarged fragmentary view of a portion of FIG. 1B.
Figure 4:
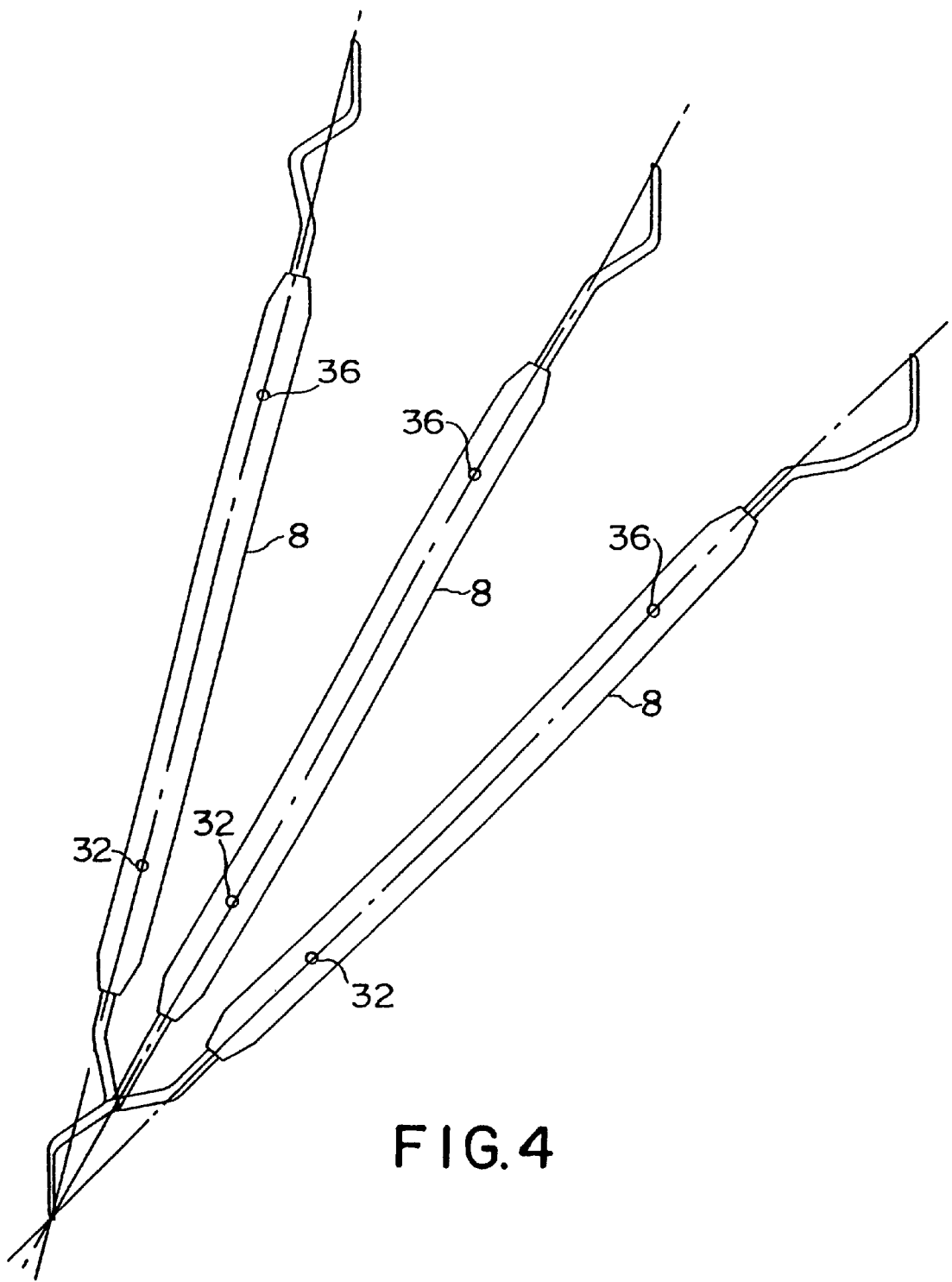
FIG. 4 is a view of three curets with different rake angles. Note that the configuration of the lower shank in the cutting blade is identical for all three instruments.

Curets. FIG. 3 shows that the cutting blade 10 of each curet 8 has a flat top surface 12 (the face), a rounded bottom surface 14 (the base), and a circular tip 16 (the toe). A shank 18, which has several bends, connects the blade to the handle 20. This particular curet is double-ended, i.e., has cutting blades in both ends. When viewed in a working position, each blade is the other's mirror image in that the toe of one blade will point to the left whereas the other will point to the right. The shank can have various configurations, but the arc center 22 of the toe on each blade's face is always located on the longitudinal center axis 24 of the instrument, i.e., the longitudinal center axis of the handle. The configuration of the lower portion 18a of the shank is identical for all curets of a particular series regardless of their rake angle, i.e., the angle between the face of the cutting blade and the long axis of the handle. The configuration of the upper half 18b of the shank determines the rake angle of the curet, and a set of curets of different rake angles facilitates access to hard-to-reach sites in the oral cavity. The upper portions of the shanks are designed to provide sets of instruments of different rake angles in regular angular increments, which are indicated by a code, e.g. color code, on the instrument handle. FIGS. 3F and 4 show three different rake angles.

The handle 20 has a circular cross-section interrupted by two opposing flat surfaces 28, 30 along almost its entire length. The handle has four circular conical depressions 32, 34, 36, and 38, which form a symmetrical pattern of reference points for the two blades. Depressions 32, 34 constitute one set of reference points and depressions 36 and 38 another set. These four reference points are arranged in the manner described earlier. The four reference points are identical, both in the pattern in which they are arranged relative to the blades and in their specific details, in all curets regardless of the configuration of their shanks, i.e., regardless of rake angle.

The junction between the face 12 and the base 14 of the blade constitutes the cutting edge 40. For proper cutting action of the curet, the edge portions 42, 44 along the sides and the end edge portion 46 around the toe must be sharpened at frequent intervals. The grinding is always done on the base surface 14 of the cutting blade, never on the face, for an edge angle of about 80 degrees. It is important to maintain the proper edge angle as well as the shape of the blade, i.e., a circular toe 16. In order to meet all these requirements, the guide unit of the sharpening machine, to be described in the next section of the text, is designed to provide guidance for the curets during the sharpening procedure.

Sharpening Machine. In the following description with illustrations, the different rotation axes are referred to as vertical or horizontal. This reference to vertical and horizontal axes is for convenience only, and a person skilled in the art would readily appreciate that it is not critical that one or the other axis be in the vertical or horizontal plane. Rather, it is the perpendicular relationship of the two axes which is important and should be maintained. Refer to FIGS. 1A–1G, and 2A–2B. The sharpening machine 50 supports two units: the electric motor 52 and the instrument guide 54. The electric motor, on the shaft 51 of which is fitted a circular rotating sharpening element 56, is disposed atop a support block 53 with the shaft at a fixed angle to the horizontal plane in order to achieve the proper edge angle of the curet's cutting blade. The motor and support block can be moved along a straight guide 58 in the base 60 of the machine toward and away from the instrument guide unit 54. It is moved away from the instrument guide unit to facilitate both the placement of the curet in the instrument guide unit before sharpening, and the removal of the curet from the instrument guide unit after sharpening. It is moved toward the instrument guide unit for the sharpening procedure.

The instrument guide unit is mounted in a ball bearing 62 housed in the base of the machine which allows the instrument guide unit to rotate in the horizontal plane about a vertical axis 64. The lower portion 66 of the instrument guide unit (the support portion) comprises one horizontal member 68 and one vertical member 70, the latter one fitted with a horizontal shaft 72 and color-coded dial 74 having a series of uniquely colored, pointed markers 75.

The upper portion 76 of the instrument guide unit (the fixture portion) rotates around the horizontal shaft 72 of the support portion, has a center line mark 78 in its lower end, and can be locked in fixed positions by means of a wing nut 80.

The fixture portion of the instrument guide unit has a lid 82 that swings around two hinges 84, 86 attached to a base 88 of the fixture portion. The opposing surfaces of lid 82 and base 88 each have a groove of semi-circular cross-section along their common longitudinal axis when the lid is closed and secured with a clamp 90, that form a tube that can securely hold and house the curet handle 20 in the fixture portion.

Proper placement of the curet is accomplished by conical pins 92, 94, 96, 98 in the lid and base of the fixture unit. The pins are arranged in a pattern matching the pattern of the reference points in the curet's handle. When the lid is clamped in a closed position, the pins fit tightly into the conical depressions 32, 34, 36, 38 in the curet handle. These reference points will guarantee a reproducible placement of the curet so that the arc center of the toe on the face of the blade to be sharpened lies on the center of the horizontal rotation axis of the fixture portion (axis of shaft 72) as well as on the center of the vertical rotation axis of the entire guide unit (axis 64). By rotating the fixture portion about the horizontal rotation axis on the instrument guide unit, the flat face of the curet can be positioned in the horizontal plane, the proper position indicated by the code, e.g. color code. This proper placement of the face of the curet for sharpening can also be accomplished using a fixture portion that has no movable placement means. Instead, the fixture portion has multiple locations at which the curet can be secured. Each location will place a curet of a particular rake angle in the proper orientation for sharpening. Curets of different rake angles will thus be secured at different locations on this type of fixture portion.

These integrated design features of the curets and sharpening machine make it possible to place a curet of any rake angle with the face of a cutting blade, which is to be sharpened, in the horizontal plane and with the center of the toe of that blade at the same time being on the rotation axis 64 of the guide unit. This will guarantee that the sharpening procedure will give exactly the same edge angle along the entire perimeter of the cutting blade and that the shape of the cutting blade, i.e., a rounded toe, will be maintained. Each unique marker color corresponds to the color of a curet of a particular rake angle so that, when a given color curet is placed in the fixture and the corresponding marker 75 aligned with marker 78, the face of the blade being sharpened is in the horizontal plane.

The electric motor unit contains a circular rod 100 which has a knob 102 at its top end. The rod 100 passes through a hole in the motor support block, and the rod's lower end contains an eccentric 104, which is cooperatively associated with a slot 106 in base 60, and parallel with guide 58. An electromagnet 110 is housed in the motor support block and a ferrous block 112 is mounted on base 60 for cooperative association with electromagnet 110.

One embodiment of the subject invention involves the use of a control means for an entirely automatic sharpening of the dental curets. This embodiment utilizes the same essential features of the sharpening machine as described above. Translational movements of the sharpening element and rotational movements of the instrument guide unit are carried out by electric motors that are powered by pulse generators. The hardware components of the control system include a central processing unit (CPU) with software stored in an erasable programmable read-only memory (EPROM), which holds the information for the execution of the program by the CPU. It is within the skill of a person trained in this art to write a program for full control of the sharpening machine using any of the following languages: C, Fortran, Pascal, or Assembly language. The program included with this application (FIG. 7) uses Assembly language, but any other language would do. The software is programmed to (1) control the strength of contact between the sharpening element and the cutting blade during the sharpening procedure; (2) establish a baseline for the sharpening procedure by assessing the position of the curet when its distal side edge is in full contact with the sharpening element; and (3) execute the sharpening cycle. A program can also be written for the sharpening of sickles, which are dental instruments of shape and function similar to those of other dental curets, the major differences being that sickles have a pointed tip, and that a section of their side edges is slightly curved.

At the beginning of the sharpening procedure, the sharpening element and the curet's cutting blade are brought into contact with each other by means of a stepping motor. The contact pressure between the sharpening element and the curet is determined by a programmed level of amperage required to keep the constant speed motor of the sharpening element at its optimal speed. A second stepping motor will then rotate the curet in the instrument guide unit, or the sharpening element, until one side edge of the curet's cutting blade is in full contact with the sharpening element. This maximum surface contact between the sharpening element and the curets cutting blade occurs when, due to the increased friction between the curet and the sharpening element, the motor of the sharpening element requires peak current to maintain its speed. The digital representation of the current to drive the motor, which is obtained by means of an analog-to-digital converter, is used to established the peak current, which determines the starting point of the sharpening cycle. The rotational movement of about 180° for sharpening the perimeter of the cutting blade is determined by the number of steps the second stepping motor will make, as programmed in the EPROM. The number of sharpening cycles for each sharpening procedure is also encoded in the software. At the end of the sharpening procedure, the first stepping motor will separate the curet and sharpening element for easy removal of the curet from the instrument guide unit.

Thus, in accordance with the teachings set forth herein, one embodiment of the subject invention is a fully automated sharpening machine comprising a base, an A/C converter, an electric pulse generator, two analog-to-digital converters, a CPU, an EPROM chip, a sliding motor with a sharpening element fitted with a replaceable grinding disc, and an instrument guide unit with a fixture unit that secures dental curets of different rake angles in the fixture so that the face of the cutting blades of the curets are in a predetermined plane, for this model the horizontal plane, with the center of the semi-circular tip (toe) of the blade coinciding with the fixture's vertical rotation axis, and said center of the semi-circular toe on the flat face of the cutting blade situated in the horizontal rotation axis of the fixture's distal (upper) arm by means of reference units (points) on the distal arm of the sharpening machine's fixture and the curets, all reference units placed according to an integrated design pattern for the sharpening machine and the curets, the CPU and EPROM establishing a baseline position of the fixture arm holding the curets for the sharpening of the instruments by sensing and determining the friction of the curets against the sharpening element and then controlling the sharpening cycle.

As used herein, the term "sharpening element" is used generically to refer to any of a number of devices for sharpening the curets. Typically, these sharpening devices will be sharpening wheels (grinding wheels) which are readily available and well known to those skilled in the art. These sharpening wheels may use a variety of sharpening surfaces that would typically consist of very fine particles such as diamond particles. The sharpening element may be fitted with a replaceable, adhesive abrasive paper or disc.

Operation. The electric motor 52 with the sharpening element 56 is moved away (position at FIG. 6A) from the instrument guide unit 54. A curet is clamped in the instrument guide unit, and the fixture portion is rotated around the horizontal shaft 72 in order to position the face 12 of the curet blade in the horizontal plane. The amount of rotation needed is easily determined by the alignment of the mark 78 on the vertical member of the fixture portion with the particular color mark 75 on the dial 74 that matches the color of the curet handle.

The rod 100 is pulled up out of the deep section 114 of the slot 106 and the motor with the sharpening element is moved toward the instrument guide unit, the tip of the rod sliding along the base of the slot, until stopped by the rod hitting the end of the slot 106 (FIG. 6B). At that point, the sharpening element is very close to, but not in contact with, the curet, and the magnet 110 in the motor unit is pulling toward the metal block 112 on the instrument base. Then, the rod is rotated to relieve the rod from the wall in the slot, and the magnet will move the motor toward the instrument guide unit until the sharpening element is in contact with one side edge of the curets cutting blade (FIG. 6C). The motor is started and the instrument guide unit is swung 180 degrees to sharpen the edge, first at one of the side edge portions 42, next the toe edge portion 46, and finally the other side edge portion 44. The pull of the magnet provides adequate pressure of the sharpening element upon the curet during the sharpening procedure. The circuitry is designed so that the power line to the electromagnet is routed through a rheostat, which is mounted between the base and the instrument guide unit. The magnet is supplied with maximum power when the sharpening element is in contact with the side edges. During the rotation of the instrument guide, when the toe of the curet is in contact with the sharpening element, less power is let through the rheostat to the electromagnet, which therefore will exert less pull. The pressure of the sharpening element on the curet's blade is preferably constant per unit length of cutting edge during the entire sharpening procedure. The motor is stopped and moved away from the curet which is then taken out of the instrument guide. Curets with the same rake angle are sharpened in sequence to minimize required adjustments of the fixture portion of the instrument guide unit for the most efficient use of the sharpening machine.

The combination of these features makes it possible to sharpen curettes with different rake angles by a simple adjustment of the sharpening machine as indicated by a suitable code, which relates to the rake angle of the curette to be sharpened, and also allows for the proper positioning of the curette. In one embodiment of the subject invention, the curettes have a code or other reference means, which facilitates identification of the rake angle and appropriate placement of the instrument in an automated sharpening machine. In a preferred embodiment, the curettes are given a bar code which identifies the rake angle of the curettes. The bar code can readily be read using standard technology well known to those skilled in the art. The curette may be marked with the bar code during the molding process, or the bar code may be added to the curette after the curette has been molded. This code makes the identification of the instrument's rake angle easy, simplifies its placement in the sharpening machine, and indicates any need for an adjustment of the sharpening machine to produce a sharp cutting edge for any one of a series of curettes having different rake angles.

Curet Usage. Curets are used most efficiently when the instrument handle is parallel with the long axis of the tooth, i.e., when the instrument's rake angle is similar to the actual rake angle relative to the root surface. This mode of instrumentation is feasible in the anterior regions of the oral cavity whereas, when working in the posterior regions, the instrument handle will be at a considerable angle to the longitudinal axis of the tooth due to interference between the instrument handle and the opposing dental arch. Consequently, instruments of different rake angles are used in different regions of the oral cavity in order to establish the optimal working rake angle for the different curets.

However, the shanks on dental curets heretofore available offer no guidance for proper angulation of the instrument relative to the longitudinal axis of the tooth to achieve the optimal working rake angle on the root surface. The innovation of this invention encompasses curets that, regardless of the instrument's rake angle, have an identical configuration of the cutting blade and lower portions of the shank, which should be positioned parallel with the root surface for optimal working rake angle.

Heretofore, dental curets have been unavailable in sets of different rake angles in regular increments, and there have been no indicators on the instruments giving the actual rake angle. Furthermore, the usually complex configuration of the shanks gives little or no guidance in positioning the curets for proper working rake angle on the root surface.

This invention presents a new concept in the design of dental curets for their compatibility with a sharpening machine providing complete mechanical guidance during the sharpening of the instruments.

CONCLUSION

The foregoing disclosure has described and exemplified a novel and unique dental curet and sharpening machine system that incorporates reference means, placement means, and control means for a fully guided and automatic sharpening of dental curets of different rake angles. The reference means and the placement means make possible the placement of the curets in the sharpening machine so that, regardless of the instrument's rake angle, their cutting blade has a predetermined orientation in space at a predetermined point in space relative to the sharpening element. The control means provide mechanical and/or electronic guidance of the curet and the sharpening means during the sharpening procedure, which assures the consistent restoration of a sharp edge of the correct angle while preserving the shape of the cutting blade.

Figures 5A, 5B:
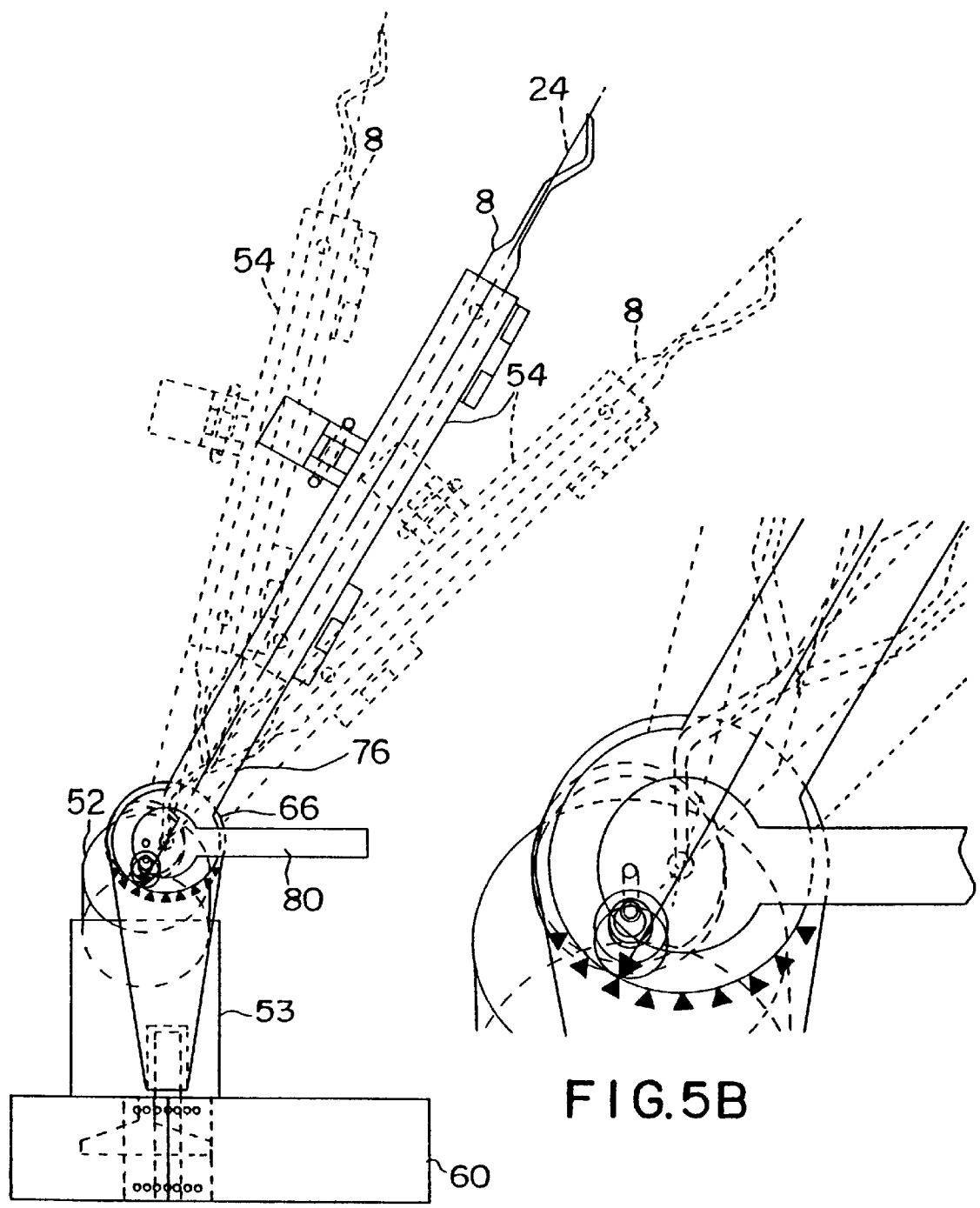
FIG. 5A is a view showing the adjustments of the fixture unit needed to put the three different curets of FIG. 4 in proper positions for the sharpening procedure.
FIG. 5B is a close-up of a portion of Figure 5A.

Although FIGS. 1A and 1D show nine different settings for nine different rake angles, the particular number of settings and dental curets in the system may be other than this particular number. FIG. 3F illustrates only three different rake angles. Likewise, FIG. 4 shows instruments of three different rake angles and FIG. 5A shows three different settings of the machine corresponding with those three different rake angles of FIG. 4. It is to be appreciated that the relative proportions illustrated in FIG. 3D are merely representative. For example, the radius of the end edge 46 and the lengths of the side edges 42, 44 are merely representative.

This disclosure exemplifies configurations of the reference means, placement means, and control means that are merely illustrative of the general principles of the invention. It is to be understood that any architecture, shape, or geometry of these means, which are used for the placement and guidance of the curets relative to the sharpening element, are claimed for this integrated dental curet/sharpening machine system.

What is claimed is:

1. A dental curette having a reference means corresponding to the rake angle of said curette wherein said reference means facilitates the sharpening of said curette in an automatic curette sharpening machine.

2. The dental curette, according to claim 1, wherein said reference means can be read by the automatic curette sharpening machine.

3. The dental curette, according to claim 1, wherein said reference means comprises a bar code.

* * * * *